(12) United States Patent
Stephenson et al.

(10) Patent No.: US 8,397,730 B2
(45) Date of Patent: Mar. 19, 2013

(54) TRACHEAL TUBE ADAPTOR AND FLARING JIG

(75) Inventors: James Stephenson, Galway (IE); James Curley, Offaly (IE)

(73) Assignee: Covidien LP, Mansfield, MA (US)

( * ) Notice: Subject to any disclaimer, the term of this patent is extended or adjusted under 35 U.S.C. 154(b) by 372 days.

(21) Appl. No.: 12/706,353

(22) Filed: Feb. 16, 2010

(65) Prior Publication Data

US 2011/0197895 A1    Aug. 18, 2011

(51) Int. Cl.
*A61M 16/00* (2006.01)
(52) U.S. Cl. .................................. 128/207.14
(58) Field of Classification Search ............. 128/207.14, 128/207.15; 285/260; 604/905, 408
See application file for complete search history.

(56) References Cited

U.S. PATENT DOCUMENTS

| | | | |
|---|---|---|---|
| 3,964,488 A | 6/1976 | Ring et al. | |
| 4,146,034 A | 3/1979 | Gupta | |
| 4,152,017 A * | 5/1979 | Abramson | 285/260 |
| 4,369,991 A | 1/1983 | Linder | |
| 4,404,159 A | 9/1983 | McFarlane | |
| 4,475,548 A | 10/1984 | Muto | |
| 4,588,402 A * | 5/1986 | Igari et al. | 604/408 |
| 4,683,879 A | 8/1987 | Williams | |
| 5,154,703 A * | 10/1992 | Bonaldo | 604/244 |
| 5,251,617 A | 10/1993 | Linder | |
| 5,333,608 A | 8/1994 | Cummins | |
| 5,487,731 A | 1/1996 | Denton | |
| 5,569,222 A * | 10/1996 | Haselhorst et al. | 604/533 |
| 5,590,647 A | 1/1997 | Nye | |
| 5,740,796 A | 4/1998 | Skog | |
| 5,906,204 A | 5/1999 | Beran et al. | |
| 6,199,421 B1 | 3/2001 | Ploeger | |
| 6,484,724 B1 | 11/2002 | Sloan | |
| 6,951,218 B2 | 10/2005 | Gradon et al. | |
| 7,156,827 B2 | 1/2007 | McNary et al. | |
| 7,293,561 B2 | 11/2007 | Madsen et al. | |
| 2003/0196659 A1 | 10/2003 | Gardon et al. | |
| 2007/0044806 A1 | 3/2007 | Madsen et al. | |

FOREIGN PATENT DOCUMENTS

WO        9824500        6/1998

OTHER PUBLICATIONS

Lee, Chao-Hsien et al.; "Dexamethasone to prevent postextubation airway obstruction in adults: a prospective, randomized, double-blind, placebo-controlled study"; Critical Care 2007; p. 1-8.
Makino, Hiroshi, MD, et al.; "The Effects of Tracheal Tube Tip Design and Tube Thickness of Laryngeal Pass Ability During Oral Tube Exchange with an Introducer"; International Anesthesia Research Society, 2003.

* cited by examiner

*Primary Examiner* — Manuel Mendez

(57) ABSTRACT

The present disclosure describes systems and methods that utilize a tracheal tube adaptor system. The tracheal tube adaptor system includes a tracheal tube adaptor and/or a flaring jig. A proximal end of a tracheal tube may be flared and the tracheal tube adaptor may be coupled to the proximal end of the tracheal tube. The tracheal tube adaptor may be configured to easily attach and detach an end connector. The end connector may be used to couple a variety of medical devices such as a ventilator, a manual respirator, a nebulizer, a vaporizer, suctioning equipment, and so forth, to the tracheal tube. The use of the tracheal tube adaptor system and methods enables the rapid detachment and attachment of various end connectors, thus allowing the coupling of the tracheal tube to a variety of medical devices.

16 Claims, 4 Drawing Sheets

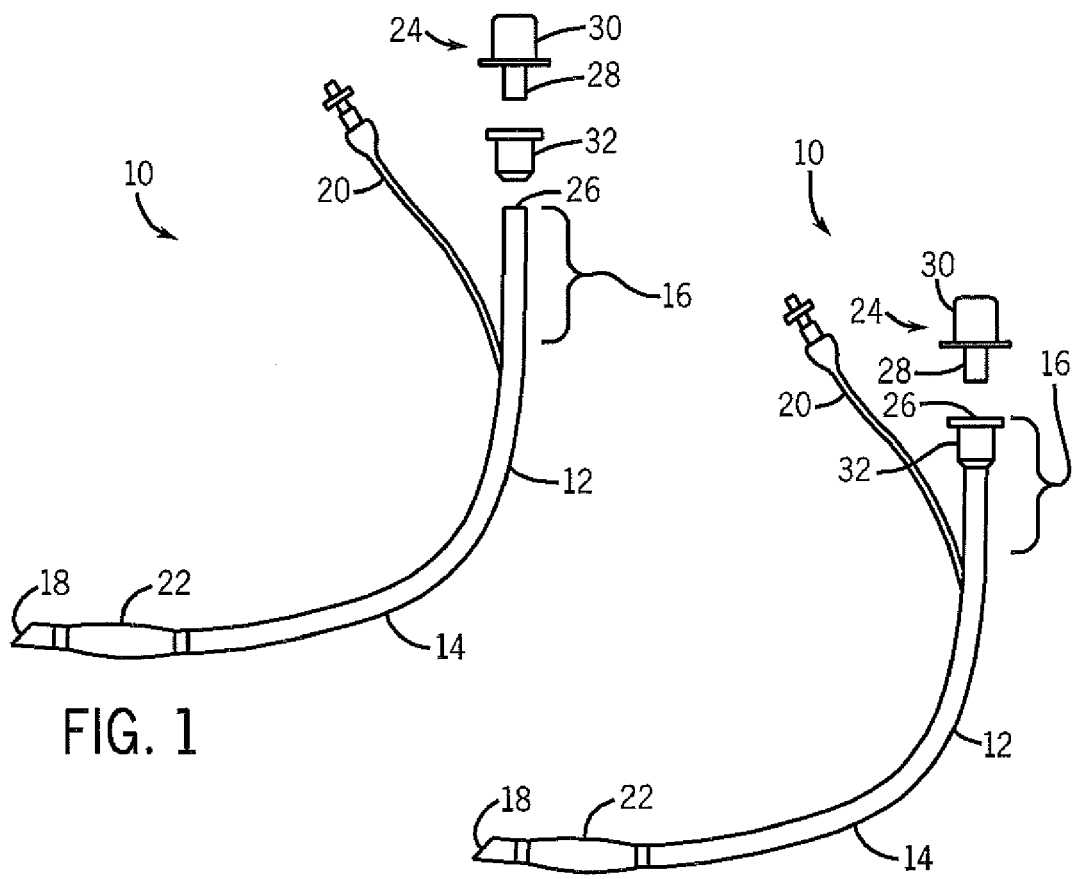
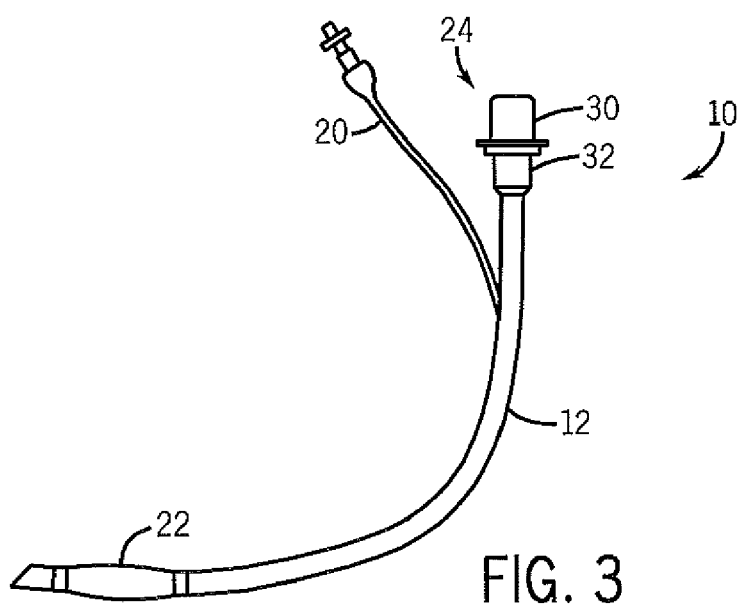

TRACHEAL TUBE ADAPTOR AND FLARING JIG

BACKGROUND

The present disclosure relates generally to tracheal tubes and, more particularly, to tracheal tube adaptors and tracheal tube flaring jigs.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the course of treating a patient, a tube or other medical device may be used to control the flow of air, food, fluids, or other substances into the patient. For example, tracheal tubes may be used to control the flow of air or other gases through a patient trachea and into the lungs during patient ventilation. Such tracheal tubes may include endotracheal (ET) tubes, tracheotomy tubes, or transtracheal tubes. In many instances, it is desirable to connect a medical device, such as a ventilator, to the patient. In this way, breathing may be artificially enhanced and monitored. Accordingly, the tracheal tube may include an end connector that may used to couple the tracheal tube to the ventilator.

However, the tracheal tube end connector may be of a size or a type that is not suitable for connection to the medical device. Removing the tracheal tube end connector and replacing the end connector with a suitable end connector can be difficult, particularly in cases where the connector is press or interference fit into the end of the tube. Typically, the end connector is removed by cutting the proximal end of the tracheal tube, leaving the tracheal tube unflared. An unflared tracheal tube makes insertion of a new connector very difficult because the tracheal tube proximal opening is typically small and rigid.

BRIEF DESCRIPTION OF THE DRAWINGS

Advantages of the disclosed techniques may become apparent upon reading the following detailed description and upon reference to the drawings in which:

FIG. 1 illustrates embodiments of a tracheal tube, a tracheal tube adaptor, and an end connector;

FIG. 2 illustrates embodiments of a tracheal tube adapter inserted in a tracheal tube, and an end connector;

FIG. 3 illustrates embodiments of a tracheal tube adapter and an end connector both inserted into a tracheal tube;

DETAILED DESCRIPTION OF SPECIFIC EMBODIMENTS

Figure 4:
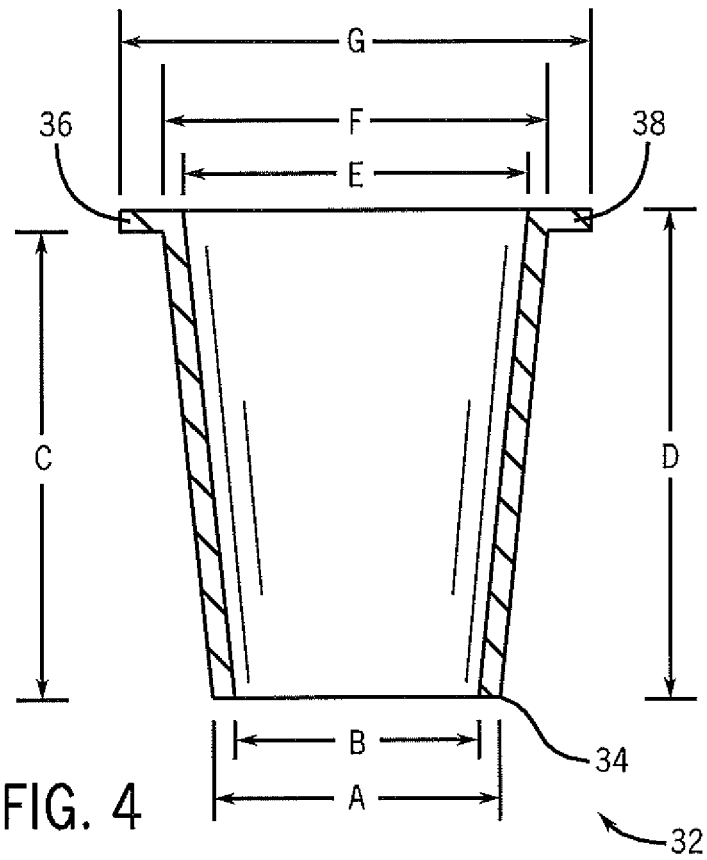
FIG. 4 is a schematic view of an embodiment of a tracheal tube adapter.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The disclosed embodiments include medical devices for artificial airway applications. In certain embodiments, a tracheal tube adaptor is provided that may be securely placed into the proximal end of a tracheal tube. The tracheal tube adapter includes a rigid material that holds the shape of the tracheal tube adapter when placed inside the tracheal tube. The tracheal tube adapter allows a standard end connector, for example, a 15 mm outer diameter (OD) end connector, to be inserted into the tracheal tube adaptor, thus allowing for rapid attachment of devices such as ventilators, manual respirators, suctioning equipment, nebulators, vaporizers, tee connectors, and so forth, to the proximal end of the tracheal tube.

In certain circumstances, for example when a patient is already intubated, a medical device such as suctioning equipment may need to be coupled to the tracheal tube. However, the medical device may have a connector sized differently or of a different type (e.g., male connector, female connector) that is not compatible with the current end connector of the patient tracheal tube. Traditionally, a clinician would have to extubate the patient and replace the tracheal tube with a tracheal tube having a suitable end connector or would have attempted to replace the end connector while the patient is intubated. In other situations, a technician or physician may wish to shorten a standard tracheal tube. In both cases, the end connector may need to be removed and replaced. Replacing the end connector typically would require cutting the tracheal tube, removing the existing end connector, and forcibly inserting a new end connector into the proximal end of the tracheal tube. However, the proximal end of the tracheal tube is not very pliant and it is generally desirable to have the connector fit very snuggly in the tube to avoid inadvertent separation of the two. Accordingly, inserting a new end connector is very difficult, even in circumstances where the tracheal tube is not in place in a patient. Accordingly, embodiments of the tube adapter described herein facilitate detachment of the end connector and attachment of a new end connector (or even the same connector), even in circumstances where the patient is intubated. Additionally, the disclosed techniques include embodiments of a flaring jig that may aid in the insertion of the tracheal tube adapter or an end connector into the tracheal tube.

With the foregoing in mind and turning now to FIG. 1, the figure depicts an embodiment of a tracheal tube system 10 that may be utilized to provide respiratory support in a patient. A tracheal tube 12, shown here as an endotracheal tube, may be inserted into a patient trachea. The tracheal tube 12 includes a distal end portion 14 and a proximal end portion 16. The distal end portion 14 is inserted into the trachea and typically includes a curved portion so as to comfortably fit inside the patient airway. In certain embodiments, the inner diameter (ID) of the tracheal tube 12 may be approximately 1 mm-20 mm, which may vary depending on whether the patient is a neonatal patient, a pediatric patient or an adult patient. The tracheal tube 12 may be any suitable length. For example, the tracheal tube 12 may be 50 mm-500 mm. A distal opening 18 may be beveled to allow for smoother insertion through the larynx and trachea. The tracheal tube 12 may also include any suitable number of lumens, such as lumen 20 that may be appropriately sized and shaped for inflation, deflation, or suction. In some embodiments, the tracheal tube 12 may include an inflatable cuff 22. When inflated, the cuff 22 generally expands into the surrounding trachea to seal the tracheal passage around the tube, for example, to facilitate the controlled delivery of gases, medicines, and other substances, via a medical device (e.g., through the tube).

Traditionally, a standard end connector 24 has been inserted into a proximal opening 26 during manufacturing to allow for the coupling of the tracheal tube 12 to medical devices such as a ventilator. The standard end connector 24 includes a lower end 28 having an OD that approximately matches the ID of the tracheal tube 12. An upper end (i.e., male connector) 30 of the end connector 24 has a standard OD (e.g., 15 mm, 8.5 mm, 8 mm) that approximately matches the ID of the medical device. Accordingly, the medical device may be coupled to the upper end 30 of the end connector 24. However, in some circumstances, a different end connector 24 is desired. For example, it may be desired to decouple the ventilator and subsequently couple another medical device having an end connector of a different size, or an end connector that presents a female attachment end instead of a male end. The old end connector 24 may be removed, for example, by cutting off a portion of the tracheal tube 12 below the end connector 24. Coupling a new end connector 24 to tracheal tube 12 is problematic due to the tight fit and the consequent amount of force required to insert the end connector lower end 28 into the proximal opening 26. Accordingly, a tracheal tube adapter 32 is disclosed that allows for ease of detachment and attachment of the end connectors 24 as described in more detail below.

In certain embodiments, such as that depicted in FIG. 2, the tracheal tube 12 is manufactured so that the tracheal tube adapter 32 is inserted into the tracheal tube 12 during the manufacturing process. For example, techniques such as machine flaring may be used in which a flaring machine employs a hydraulic or other actuator and a flaring die to flare the proximal opening 26 of the tracheal tube 12. A robotic device or a human operator may then insert the tracheal tube adaptor 32 into the proximal opening 26 of the tracheal tube 12. Accordingly, the tracheal tube 12 arrives at a clinical location with the tracheal tube adapter 32 inserted into the proximal opening 26. In other embodiments, the tracheal tube 12 does not have the tracheal tube adapter 32 inserted during manufacturing. The tracheal tube adapter 32 may then be inserted into the tracheal tube 12, for example, by using embodiments of a flaring jig as described in more detail with respect to FIG. 5 below. Once inside the tracheal tube 12, the tracheal tube adaptor 32 may be securely coupled to the tracheal tube 12 by a strong interference fit. That is, the compressive forces applied to the connector by the tube results in a frictional force between the outside walls of the tracheal tube adaptor 32 and the inside walls of the tracheal tube 12 to provide a very tight coupling between the tracheal tube adaptor 32 and the tracheal tube 12.

Once the tracheal tube adapter 32 is inserted into the tracheal tube 12, the lower end 28 of the end connector 24 may be inserted into the tracheal tube adapter 32 as depicted in FIG. 3. The resulting tracheal tube system 10 may then be used to provide respiratory support in a patient, for example, by coupling a ventilator to the upper end 30 of the end connector 24. However, the force of the interference fit between the end connector 24 and the tracheal tube adaptor 32 is less than the force of the interference fit between the tracheal tube adaptor 32 and the tracheal tube 12. Accordingly, an extraction force, for example an extraction force exerted by pulling axially on the upper end 30 of the end connector 24, will cause the end connector 24 to decouple from the tracheal tube adaptor 32 while the tracheal tube adaptor 32 remains coupled to the tracheal tube 12. Indeed, the disclosed embodiments allow for the manual decoupling of the end connector 24 while maintaining a secure coupling of the tracheal tube adaptor 32 to the tracheal tube 12. Further, the disclosed embodiments, such as the embodiments described in more detail with respect to FIG. 4 below, allow for the manual coupling of a new end connector 24 having the upper end 30 in a different size or type (e.g., male connector, female connector).

FIG. 4 is a cross-sectional view of an embodiment of a the tracheal tube adaptor 32 that allows for ease of coupling and decoupling various end connectors 24 while maintaining a secure coupling with the tracheal tube 12. As mentioned above, the tracheal tube adaptor 32 may be inserted into the proximal opening 26 of the tracheal tube 12 and is capable of maintaining a secure coupling with the tracheal tube 12. The tracheal tube adaptor 32 also allows for the insertion of the end connector 24 into the tracheal tube adapter 32 such that an end connector extraction force capable of extracting the standard end connector 24 from the tracheal tube adaptor 32 is less than a tracheal tube adaptor extraction force capable of extracting the tracheal tube adaptor 32 from the tracheal tube 12. Accordingly, the tracheal tube adaptor 32 may include certain measurements (e.g., A, B, C, D, E, F, G), such as those measurements depicted in FIG. 4, that may result in a strong interference fit with the tracheal tube 12 but that allow for ease in coupling and decoupling of the end connector 24.

TABLE 1

| End Connector OD | A | B | C | D | E | F | G |
|---|---|---|---|---|---|---|---|
| 3.0 mm | 4.47 mm | 4.07 mm | 12.58 mm | 12.78 mm | 4.10 mm | 4.50 mm | 4.70 mm |
| 4.0 mm | 5.46 mm | 5.06 mm | 12.58 mm | 12.78 mm | 5.08 mm | 5.48 mm | 5.68 mm |
| 4.5 mm | 5.47 mm | 5.57 mm | 12.58 mm | 12.78 mm | 5.60 mm | 6.00 mm | 6.20 mm |
| 5.0 mm | 6.07 mm | 6.07 mm | 12.58 mm | 12.78 mm | 6.10 mm | 6.50 mm | 6.70 mm |
| 5.5 mm | 6.48 mm | 6.58 mm | 12.58 mm | 12.78 mm | 6.60 mm | 7.00 mm | 7.20 mm |

Table 1 above contains exemplary values for the depicted measurements A-G that may be used by certain exemplary embodiments of the tracheal tube adaptor 32. More specifically, the table contains a series of measurements that may be used to manufacture the tracheal tube adaptor 32 based on the OD of the lower end 28 (i.e., "End Connector OD" column) of the end connector 24. Standard end connectors, such as the end connector 24, are typically manufactured so that the OD of their lower end 28 is capable of insertion into a tracheal tube 12 having a particular ID. Tracheal tubes 12 may have IDs ranging from 1.0 mm to upwards of 8 mm based on patient type (e.g., neonatal, pediatric, adult) and/or other factors. Accordingly, Table 1 lists five rows of measurements, each row corresponding to a different size of the lower end 28 OD of an end connector 24. It is to be understood that other values for the A-G measurements, for example, values having a range of ±1%, ±5%, ±10%, or ±15% from the values disclosed in Table 1, may be used that also result in as secure coupling between the tracheal tube adaptor 32 and the tracheal tube 12 while allowing for ease of coupling and decoupling of the end connector 24 from the tracheal tube adaptor 32. It is also to be understood that while Table 1 contains five rows of measurements corresponding to the values 3.0 mm, 4.0 mm, 4.5 mm, 5.0 mm, and 5.5 mm, other sizes and dimensional relationships may also be utilized.

A description of the measurements A-G depicted in FIG. 4 is as follows. A is the measurement of an OD of a lower end 34 of the tracheal tube adaptor 32. B is the measurement of an ID of the lower end 34 of the tracheal tube adaptor 32. C is the measurement of a length from the lower end 34 to a flange 36. D is the measurement of a length from the lower end 34 to an upper end 38 of the tracheal tube adaptor 32. E is the measurement of an ID of the upper end 38. F is the measurement of an OD of the upper end 38. G is the measurement of a length from the OD of the upper end 38 to the end of the flange 36. Accordingly the lower end 34 of the tracheal tube adaptor 32 may be coupled to the tracheal tube 12 while the upper end 36 of the tracheal tube adaptor 32 may be coupled to the end connector 24.

Embodiments of the tracheal tube adaptor 32 may be manufactured to include the measurements A-G by using a plurality of techniques, for example, injection molding, extrusion manufacturing, computer numerical control (CNC) milling, casting, and so forth. In some embodiments, the tracheal tube adaptor 32 may be manufactured out of a material having a hardness of approximately 80-90 Shore A. Some example materials that may be used in the manufacture of the tracheal tube adaptor 32 include polypropylene, polyvinyl chloride (PVC), and acrylonitrile butadiene styrene (ABS). The resulting relative rigidity of the tracheal tube adaptor 32 prevents the walls of the tracheal tube 12 from compressing inwardly when the tracheal tube adaptor 32 is in place. The rigid property of the tracheal tube adaptor 32 also aids in the ease of coupling and decoupling of the end connector 24 by minimizing the effects on the end connector 24 of the compressive forces exerted by the walls of the tracheal tube 12.

Figure 5:
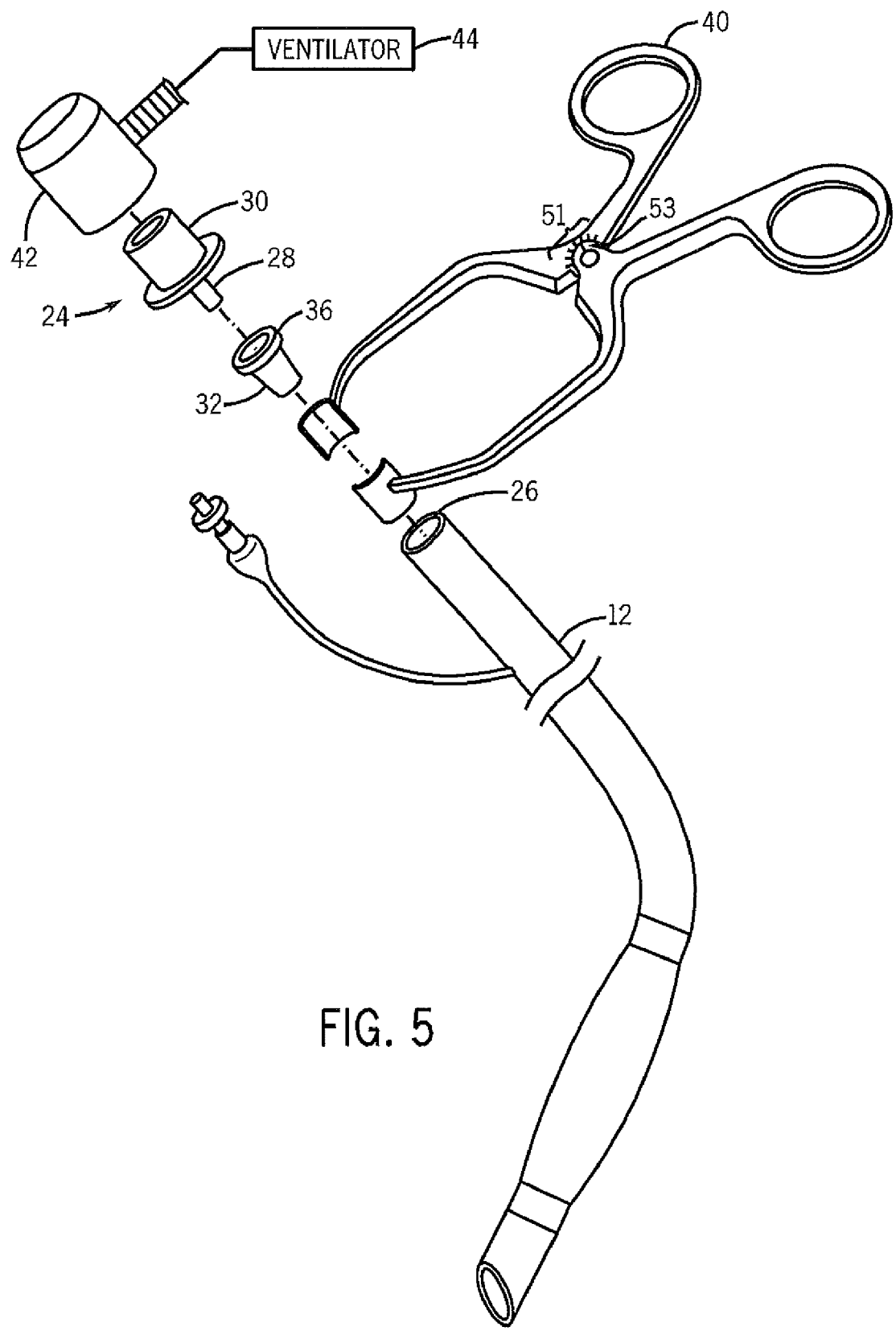
FIG. 5 is a perspective view of embodiments of a tracheal tube, a flaring jig, a tracheal tube adapter, and an end connector.

FIG. 5 illustrates embodiments of the tracheal tube 12, a flaring jig 40, the tracheal tube adaptor 32, and the end connector 24. In certain circumstances where the tracheal tube 12 does not include a tracheal tube adaptor 32, the clinician may desire to exchange an existing end connector 24 for a different end connector 24. Accordingly, the clinician may cut off a portion of the tracheal tube 12 containing the old end connector 24. The flaring jig 40 may then be inserted in the proximal opening 26 of the tracheal tube 12 and used to flare (i.e., enlarge) the proximal opening 26. In certain embodiments, the flaring jig 40 may include a flaring measurement system (e.g., measurement grooves 51 and a flare indicator 53) that may be used to obtain a desired diameter for the enlargement of the proximal opening 26 as described in more detail with respect to FIGS. 6 and 7 below. Once the proximal opening 26 has been flared, the tracheal tube adaptor 32 may be manually inserted into the proximal opening 26, for example, by exerting an axial force that is capable of driving the tracheal tube adaptor 32 into the tracheal tube 12. The flange 36 of the tracheal tube adaptor 32 is able to prevent over-insertion of the tracheal tube adaptor 32. That is, the flange 36 stops the tracheal tube adaptor 32 from being inserted too deeply inside of the tracheal tube 12 by contacting the edges of the proximal opening 26, thus stopping further insertion. It is also to be understood that the flaring jig 40 may be used to insert a new end connector 24 into the tracheal tube 12. Indeed, the flaring jig 40 allows for the insertion of either the tracheal tube adaptor 32 or the end connector 24 into the proximal opening 26.

If the tracheal tube adaptor 32 has been inserted into the tracheal tube 12, the lower end 28 of the end connector 24 may then be inserted into the tracheal tube adaptor 32. Indeed, end connectors 24 having different upper ends 30, including standard end connectors 24 having upper ends (e.g., male adaptor) 30 with ODs of 15 mm, 8.5 mm, 8 mm, and so forth, may be inserted into the tracheal tube adaptor 32. The end connector 24 may then be coupled, for example, to a female end connector 42 of a ventilator 44. In the depicted embodiments, the coupling with the ventilator 44 is possible because the female end connector 42 of the ventilator 44 has an ID appropriately sized to match the OD of the upper end 30 of the end connector 24. It is advantageous to have the tracheal tube adaptor 32 inserted into the tracheal tube 12 because the tracheal tube adaptor 32 allows for the coupling and decoupling of various end connectors 24 as needed. Indeed, the tracheal tube adaptor 32 allows a clinician to rapidly change the end connector 24 any number of times as needed, with reasonable effort without resort to special tools or appliances other than as described.

Figure 6:
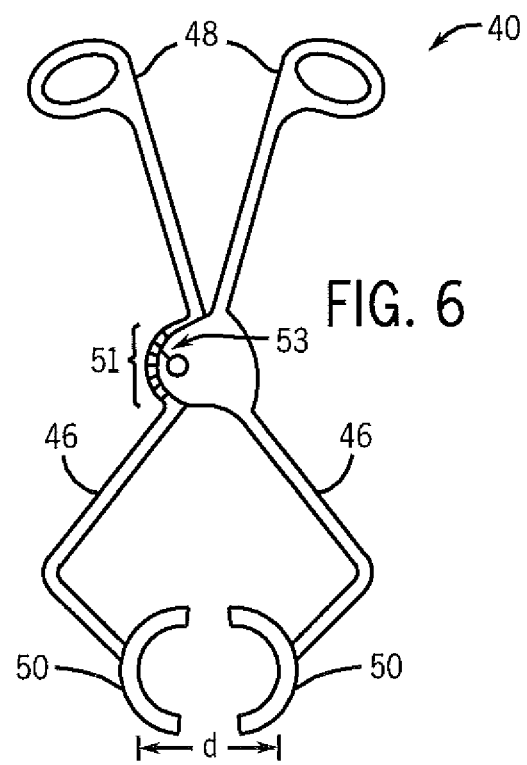
FIG. 6 is a top view of an embodiment of a flaring jig.

FIG. 6 is a top view of an embodiment of an exemplary flaring jig 40. The flaring jig 40 may be included as part of a kit (e.g., connector replacement kit) that also includes, for example, one or more tracheal tube adaptors 32. In the depicted embodiment, the flaring jig 40 is a reverse fulcrum flaring jig 40. That is, the front arms 46 of the flaring jig 40 are capable of opening when the two handles 48 of the flaring jig 40 are brought together (i.e., closed). In other embodiments, the flaring jig 40 may have a standard fulcrum so that the front arms 46 of the flaring jig 40 are capable of opening when the two handles 48 of the flaring jig are brought apart (i.e., opened). In the depicted embodiment, each arm 46 of the flaring jig 40 includes a curved wall 50. The two curved walls 50, when brought together, may form an approximately circular shape having an outer diameter d. In other embodiments, the curved walls may form other shapes such as an oblong shape or an oval shape. The outer diameter d is sized so as to allow the insertion of the curved walls 50 into the proximal end 26 of the tracheal tube 12 with relative ease. In certain embodiments, a flaring measurement system may be included in the flaring jig 40. For example, the plurality of measurement grooves 51 and the corresponding flare indicator 53 may be included on the flaring jig 40. The measurement grooves 51 may be capable of visually displaying diameter measurements corresponding to the ID of the tracheal tube 12, for example, 3 mm, 4 mm, 4.5 mm, 5 mm, and so forth. That is, the displayed diameter of 3 mm is capable of flaring a tracheal tube 12 that has a 3 mm ID, the displayed diameter of 4 mm is capable of flaring a tracheal tube 12 that has a 4 mm ID, and so forth. The flare indicator 53 indicates the currently selected diameter. A clinician may thus choose a displayed diameter on the flaring jig 40 that corresponds to the ID of the tracheal tube 12 in order to obtain a suitable flaring. Accordingly, it may be possible to flare the proximal opening 26 of the tracheal tube 12 at a suitable flaring diameter by using one hand to hold the tracheal tube 12 and a second hand to hold the flaring jig 40. The second hand may insert the flaring jig curved walls 50 into the proximal opening 26, and then close the handles 48 of the flaring jig 40 until the flare indicator 53 reaches the desired diameter as visually indicated by the corresponding measurement grove 51. The closing of the handles 48 of the flaring jig 40 thus results in the flaring of the tracheal tube 12 as described in more detail below respect to FIG. 7.

Figure 7:
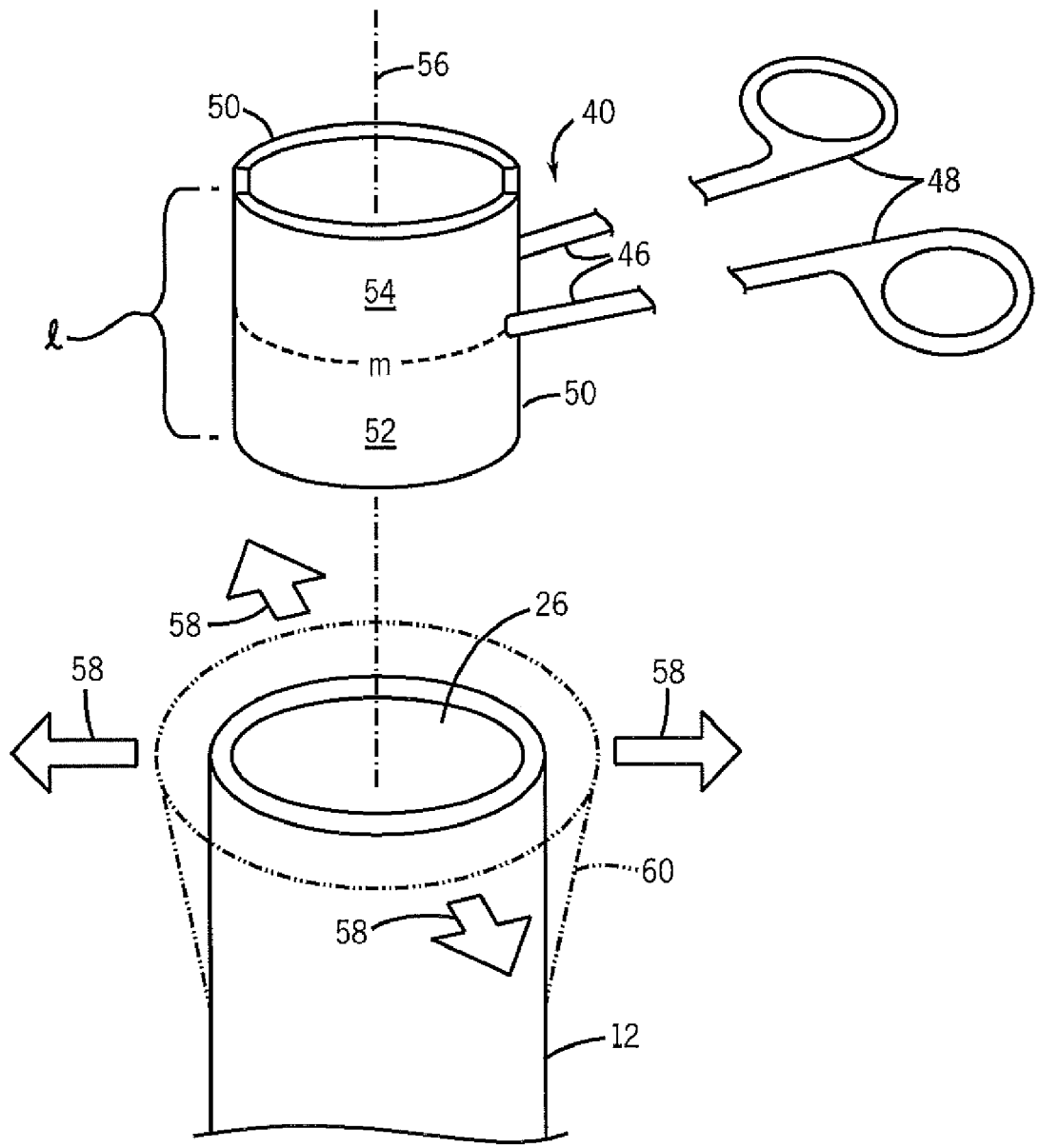
FIG. 7 is a perspective view of embodiments of a flaring jig and a proximal end of a tracheal tube.

FIG. 7 is a perspective view depicting a flaring of the tracheal tube 12 by using embodiments of the flaring jig 40. In the depicted embodiment, the flaring jig 40 includes a set of curved walls 50 having a length l. An end 52 is positioned so as to face towards the proximal opening 26 of the tracheal tube 12 and an end 54 is positioned so as to face away from the proximal opening 26. Each of the curved walls 50 has an arm 46 attached to the curved wall 50 at a midpoint of m=l/2. Accordingly, the flaring jig 40 is a symmetrical flaring jig 40 having no preferential insertion orientation. That is, the flaring jig 40 may be used such that either of the ends 52 or 54 may be inserted into the tracheal tube 12 and used for the flaring of the tracheal tube 12. In other embodiments, the flaring jig 40 may not be a symmetrical flaring jig 40 and may have an end 52 or an end 54 that is to be used as the insertion end in flaring the tracheal tube 12. In this embodiment, an end such as the end 52 may have a longer length than the opposing end 54 and may thus be used as the preferred insertion end.

The curved walls 50 of the flaring jig 40 may be inserted into the proximal opening 26 so that the curved walls 50 share a common longitudinal axis 56 with the tracheal tube 12. Once inside the proximal opening 26, the handles 48 of the flaring jig 40 may be used to cause the curved walls 50 to move apart radially. Accordingly, the curved walls 50 will exert a radial force 58, causing the walls of the proximal end of the tracheal tube 12 to extend outwardly. The outward extension of the walls of tracheal tube 12 will result in a flare 60 of the tracheal tube 12. As described above with respect to FIG. 6, the flaring measurement system (e.g., measurement grooves 51 and flare indicator 53) may be used to arrive at a desirable flaring diameter for the flare 60. Indeed, by using the measuring grooves 51 and the flare indicator 53 it may be possible to quickly and accurately flare the proximal opening 26 of the tracheal tube 12. The flare 60 includes a larger proximal opening 26 than when the tracheal tube 12 was left unflared. Accordingly, the tracheal tube adaptor 32 may be easily inserted, for example, by manually driving the tracheal tube adaptor 32 into the tracheal tube 12 through the proximal opening 26.

The tracheal tube 12 may be manufactured out of an elastic or semi-elastic material such as polyvinyl chloride (PVC), polyurethane, polyethylene teraphthalate (PETP), low-density polyethylene (LDPE), polypropylene, silicone, neoprene, polytetrafluoroethylene (PTFE), or polyisoprene, that is capable of flexing outwardly when a radial force such as force 58 is applied and then returning inwardly to approximately its original position once the radial force 58 is removed. Accordingly, once the tracheal tube adaptor 32 is placed inside the proximal opening 26, the walls forming the proximal opening 26 will attempt to return to the original diameter of the proximal opening 26. Such an elastic property will create a compressive force that results a frictional component that aids in maintaining a secure coupling between the tracheal tube adaptor 32 and the tracheal tube 12. Indeed, the coupling between the tracheal tube adaptor 32 and the tracheal tube 12 is stronger than the coupling between the end connector 24 and the tracheal tube adaptor 32, enabling for the manual removal of the connector 24 while allowing for the secure coupling of the tracheal tube adaptor 32 to the tracheal tube 12. Embodiments of the tracheal tube adapter and flaring jig described herein facilitate the detachment of the end connector and the attachment of a new end connector (or even the same connector), even in circumstances where the patient is intubated.

What is claimed is:

1. A tracheal tube adaptor system comprising:
  a tracheal tube adaptor comprising an upper end and a lower end, wherein the lower end is configured to be coupled to a tracheal tube and the upper end is configured to be coupled to an end connector comprising an end connector lower end, wherein a first extraction force required to decouple an interference fit of the end connector from the tracheal tube adaptor is less than a second extraction force required to decouple the tracheal tube adaptor from the tracheal tube, wherein the tracheal tube adaptor comprises a tapered body having the upper end and the lower end, and wherein the upper end comprises an upper end opening having a size suitable for the insertion of the end connector lower end inside of the tapered body.

2. The system of claim 1, wherein the end connector comprises a male end connector having an outer diameter sized to fit inside of a female end of a ventilator connector for use during mechanical ventilation.

3. The system of claim 2, wherein the outer diameter comprises approximately 15 mm and the upper end opening size is smaller than approximately 15 mm.

4. The system of claim 1, wherein the end connector comprises a female end connector.

5. The system of claim 1, wherein the tracheal tube adaptor comprises a polypropylene, a polyvinyl chloride (PVC), an acrylonitrile butadiene styrene (ABS), or a combination thereof.

6. The system of claim 1, wherein the tracheal tube adaptor comprises a hardness of at least approximately 80 Shore A.

7. The system of claim 1, wherein the tracheal tube adaptor comprises an inner diameter of at least 1 mm.

8. The system of claim 1, wherein the tracheal tube adaptor comprises an outer diameter of at least 2 mm.

9. The system of claim 1, wherein the tracheal tube comprises an inner diameter of at least 2 mm.

10. A tracheal tube adaptor system comprising:
  a tracheal tube adaptor configured to be coupled to a tracheal tube;
  an end connector configured to be coupled to the tracheal tube adaptor or to the tracheal tube; and,
  a tracheal tube flaring device configured to flare the tracheal tube.

11. The system of claim 10, wherein the tracheal tube adaptor is manufactured of polypropylene, polyvinyl chloride (PVC), acrylonitrile butadiene styrene (ABS), or a combination thereof.

12. The system of claim 10, wherein the tracheal tube adaptor is coupled to the tracheal tube.

13. The system of claim 12, wherein the end connector is coupled to the tracheal tube adaptor.

14. The system of claim 10, wherein the end connector is coupled to the tracheal tube.

15. The system of claim 10, wherein the flaring device comprises a reverse fulcrum flaring jig.

16. The system of claim 10, wherein at least the tracheal tube adapter and the flaring device comprise a connector replacement kit.

* * * * *